United States Patent
Van Saarloos

(10) Patent No.: US 7,715,451 B2
(45) Date of Patent: May 11, 2010

(54) HOUSING FOR HARMONIC GENERATION CRYSTALS IN SOLID STATE LASER SYSTEMS

(75) Inventor: Paul Philip Van Saarloos, Gwelup (AU)

(73) Assignee: CustomVis PLC, Balcatta (AU)

( * ) Notice: Subject to any disclaimer, the term of this patent is extended or adjusted under 35 U.S.C. 154(b) by 50 days.

(21) Appl. No.: 11/547,539

(22) PCT Filed: Mar. 29, 2005

(86) PCT No.: PCT/AU2005/000450

§ 371 (c)(1),
(2), (4) Date: May 21, 2007

(87) PCT Pub. No.: WO2005/096090

PCT Pub. Date: Oct. 13, 2005

(65) Prior Publication Data

US 2007/0223541 A1 Sep. 27, 2007

(30) Foreign Application Priority Data

Mar. 31, 2004 (AU) .............................. 2004901714

(51) Int. Cl.
H01S 3/10 (2006.01)
(52) U.S. Cl. ............................. 372/21; 372/22; 359/362
(58) Field of Classification Search .................... 372/21, 372/22; 359/326
See application file for complete search history.

(56) References Cited

U.S. PATENT DOCUMENTS

| 3,449,147 | A | * | 6/1969 | Schaffer et al. | ................ 117/99 |
| 3,617,804 | A | * | 11/1971 | Paine et al. | .................. 315/326 |
| 6,002,697 | A | | 12/1999 | Govorkov et al. | |
| 6,532,100 | B1 | | 3/2003 | Partanen et al. | |
| 6,723,977 | B1 | * | 4/2004 | Fukumoto | .................... 250/216 |
| 7,136,403 | B2 | * | 11/2006 | Reid et al. | ..................... 372/22 |

FOREIGN PATENT DOCUMENTS

| JP | 04100285 | * | 4/1992 |
| JP | 07-15061 | | 1/1995 |
| JP | 11-71820 A | | 10/1999 |
| WO | WO02/33484 | * | 4/2002 |

* cited by examiner

Primary Examiner—Armando Rodriguez
Assistant Examiner—Delma R Forde
(74) Attorney, Agent, or Firm—Stephen A. Bent; Foley & Lardner LLP

(57) ABSTRACT

Apparatus for effecting harmonic conversion of a laser beam of predetermined frequency, to provide plural harmonic components of the laser beam at frequencies different from the predetermined frequency, includes a housing (40) defining a hermetically sealed chamber able to be maintained at a pressure below atmospheric pressure. Also provided are port means for evacuating the chamber, and means (36, 37) defining an optical path for the laser beam and the components thereof through the housing and the chamber. A plurality of individual holders (70, 72, 74) are arranged for retaining respective frequency conversion crystals at spaced locations in the optical path. The crystals (20, 22, 24) can be aligned individually and heated within the chamber.

12 Claims, 5 Drawing Sheets

HOUSING FOR HARMONIC GENERATION CRYSTALS IN SOLID STATE LASER SYSTEMS

FIELD OF THE INVENTION

This invention relates generally to the housing of frequency conversion crystals in solid state laser systems, and as such has particular though not exclusive application in solid state laser systems for generating laser beams of wavelengths suitable for photo-ablation of materials. Such laser beams have widespread application in the surgical and medical fields, including operations for correcting refractive errors of the eye.

BACKGROUND ART

Excimer gas lasers remain the principal laser system of choice for refractive eye surgery by photo-ablation, in which corneal eye tissue is vaporised while causing little or no thermal damage to adjacent areas. Notwithstanding their widespread use, excimer lasers have a number of inherent disadvantages, including large size and high operating and maintenance costs, and reliance on a gas that must be regularly replaced and is extremely toxic and therefore dangerous to ship and handle. Excimer lasers have an operating wavelength of 193 nm, in the ultraviolet region of the electromagnetic spectrum.

Alternative solid state laser systems have been proposed for generating an ultraviolet laser beam, suitable for corneal ablation, by frequency conversion of the output of an infrared solid state laser, such as the widely used neodymium:YAG laser. The Nd:YAG laser produces a wavelength of 1064 nm, and this output beam is directed through a sequence of non-linear optical (NLO) crystals to derive an appropriate harmonic in the ultraviolet region by a process known as harmonic generation. Such systems are generally described in, eg U.S. Pat. Nos. 5,144,630 and 5,592,325. U.S. Pat. No. 6,381,255 discloses a solid state laser system in which an Nd:YAG laser beam is passed in sequence through a crystal of beta barium borate ($\beta$-BaB$_2$O$_4$ or BBO) and a pair of crystals of caesium lithium borate (CsLiB$_6$O$_{10}$ or CLBO) to generate the fifth harmonic of the Nd:YAG laser output at 213 nm, which has been found to be especially suitable for refractive surgery by photo-ablation. This harmonic has also been produced using three BBO crystals (Lago et, 1988, Optics Letters 13(3): 221-223).

For the harmonic generation process to work properly, the laser beam must pass through the non-linear crystal at exactly the right angle relative to the crystal structure. A very small error in the angle that the laser beam passes through the crystal can cause the conversion efficiency to drop significantly, possible even to zero. Fundamental problems arise from this sensitivity to angular presentation. Firstly, the exact required angle through the crystal usually depends on the temperature of the crystal and temperature gradients within the crystal. Secondly, the crystal usually absorbs a little of either or both the incident longer wavelength and the newly generated harmonic shorter wavelength. This absorbed laser energy heats the crystal, changing its temperature and creating temperature gradients within the crystal. Thus, the required angle through the crystal for efficient harmonic generation when the crystal is cold, ie. at the time the laser has just been switched on, is different from the required angle when the laser has been running for a while and its heating of the crystal has reached a steady state.

When a laser is first switched on and the laser beam passes through the crystal at the angle required for warm steady state efficient harmonic generation, it is not unusual for there to be no harmonic generation at all. In such an instance, the harmonic wavelength cannot contribute to heating of the crystal, and therefore the temperature state of the crystal that produces any harmonic generation is never reached. Even when the differences in angles between the cold starting condition and the warm steady state condition are not sufficient enough to create the problem described above, the changes in optimum angle do create long warm-up times and potentially large swings in the energy of the generated harmonic wavelength. To reach the fourth or fifth harmonic, for example 266 nm or 213 nm for an Nd:YAG system, the conversion process usually requires two or three crystal stages respectively. The instabilities of energy are thus multiplied for these shorter wavelengths.

Because of these difficulties, solid state wavelength laser sources have to date generally been considered unsuitable for industrial or medical applications.

The aforementioned U.S. Pat. No. 6,381,255 discloses arrangements for mounting the frequency conversion crystals in hermetically sealed housings with in-built heater elements for maintaining the crystals at optimum temperatures, which is important for the stability of the frequency conversion process. In one embodiment, the two CLBO crystals are mounted together in optical contact in the one housing, while in the other they are mounted in separate housings.

U.S. Pat. No. 6,381,255 also proposes keeping the laser pulse repetition rate low to allow the crystal to cool and partially return to its initial state between pulses. However, in many industrial applications the low pulse repetition rate makes the application uneconomic due to slow material processing rates. Even in the medical applications of laser refractive surgery, such a low pulse repetition rate can lead to impractically long treatment times. This is particularly true in the new types of treatments based on topography or wavefront linked customised ablations that require many smaller pulses to be applied to the cornea. Furthermore, with improvements in diode lasers in recent times there is now a preference that solid state lasers are diode laser pumped instead of flash-lamp pumped. Diode laser pumped solid state lasers are potentially more reliable and have better energy stability in their infrared laser output than flash-lamp pumped solid state lasers. However, diode laser pumped systems are inefficient at the low pulse repetition rates proposed in U.S. Pat. No. 6,381,255.

Australian patent application 30076/89 proposes an arrangement of two or more optical crystals inside the laser resonator cavity. Each crystal has an individual temperature controller to adjust the temperature of the crystal for optimising performance. The orientation of each crystal is also adjusted to optimise performance.

To address small fluctuations in the direction of the laser beam as it emerges from the crystal, European patent publication 1 041 427 discloses a crystal holder fitted with "beam passage components" adjacent the incident and exit faces of the CLBO crystal to reduce localised air shimmer arising from the crystal heating system. In another arrangement disclosed in European patent publication 1 048 974, which is also concerned with reducing crystal interface degradation, elongate hermetically sealed spaces extend from the respective crystal housing windows, and these spaces are filled with high purity oxygen or a gas mixture of high purity oxygen and an inert gas.

International patent publication WO 02/33484 discloses an arrangement in which three OPO crystals are mounted within a common housing in respective holders that are rotatable for individual fine rotational adjustment of the crystals about respective axes. Individual Peltier heating elements are mounted in association with the respective holders for controlling the temperatures of the respective crystals.

U.S. Pat. No. 6,002,697 addresses the problem at hand by proposing mounting each of the three non-linear frequency conversion crystals in a separate sealed housing that is either purged with inert gas at a slight positive pressure or evacuated, to remove moisture from the housing and thereby prevent its contamination of the crystal. The temperature of each crystal is maintained at about "100° C. or more" by a heater in a feedback loop that includes a temperature sensor at the crystal. Tilt adjustment is by a set screw acting externally on the housing, which is rotationally supported.

Reference in the preceding discussion to particular patent documents or other publications is not to be taken as an admission that the disclosures therein are common general knowledge in Australia or elsewhere.

This invention is primarily directed to the provision of solid state laser systems of enhanced beam stability and uniformity, and with a longer crystal life than presently observed.

SUMMARY OF THE INVENTION

It has been appreciated, in accordance with the invention, that at least partial resolution of the aforementioned difficulties lies in housing all of the crystals of a set at an elevated temperature in a sustained vacuum, whereby to prevent cyclic re-absorption of water vapour by the crystals.

The invention accordingly provides, in one aspect, apparatus for effecting harmonic conversion of a laser beam of predetermined frequency to provide plural harmonic components of the laser beam at frequencies different from said predetermined frequency, including:

- a housing defining a hermetically sealed chamber able to be maintained at a pressure below atmospheric pressure;
- port means for evacuating said chamber;
- means defining an optical path for said laser beam and said components thereof through said housing and said chamber; and
- a plurality of individual holders for retaining respective frequency conversion crystals at spaced locations in said optical path.

Preferably, there is further provided means for heating each of said crystals individually in said chamber, means for monitoring the temperature of each crystal, electrical communication lines for communicating said heating means and monitoring means to the exterior of the housing, and hermetic access porting through which said communication lines pass substantially without diminishing the vacuum in said chamber.

In an embodiment, said individual holders for the crystals are individually rotatable to finely adjust the orientations of the respective crystals.

The crystals are conveniently non-linear optical (NLO) crystals, and typically include one or more CLBO crystals.

Each of said holders preferably includes means for clamping its respective crystal in at least two directions, most preferably one perpendicular to the optical alignment and the other substantially coaxial with or at least parallel to the optical alignment. The clamping means is advantageously arranged to minimise stress on the crystal and preferably to distribute the clamping force over a large area of the crystal.

Preferably, there are three holders in an arrangement for providing three crystals for deriving, from an infra-red beam, an ultra-violet beam, eg around 213 nm, suitable for photo-refractive ablation of biological tissue. An especially effective arrangement is a lithium borate (LBO) crystal followed by two caesium lithium borate (CLBO) crystals, in which the axis about which said rotational adjustment is made for the middle CLBO crystal extends orthogonally with respect to the other two axes of adjustment, and both of these axes are orthogonal to the optical alignment. Alternative crystal arrangements are of course possible and envisioned by the present invention.

The housing is preferably a double-sealed housing having said chamber containing the crystals and an outer sub-chamber, which chambers are separately hermetically sealed.

The apparatus of the invention may be included in a laser beam generation system that includes laser means, preferably solid state laser means, for generating said laser beam. Optics may be provided as necessary to direct the generated laser beam to the apparatus of the invention.

In a particularly advantageous embodiment, the apparatus of the invention is provided as part of laser ablation apparatus, eg apparatus for performing refractive eye surgery by photoablation of corneal or other eye tissue.

BRIEF DESCRIPTION OF THE DRAWINGS

The invention will now be more fully described, by way of example only, with reference to the accompanying drawings, in which.

PREFERRED EMBODIMENTS

Figure 1:
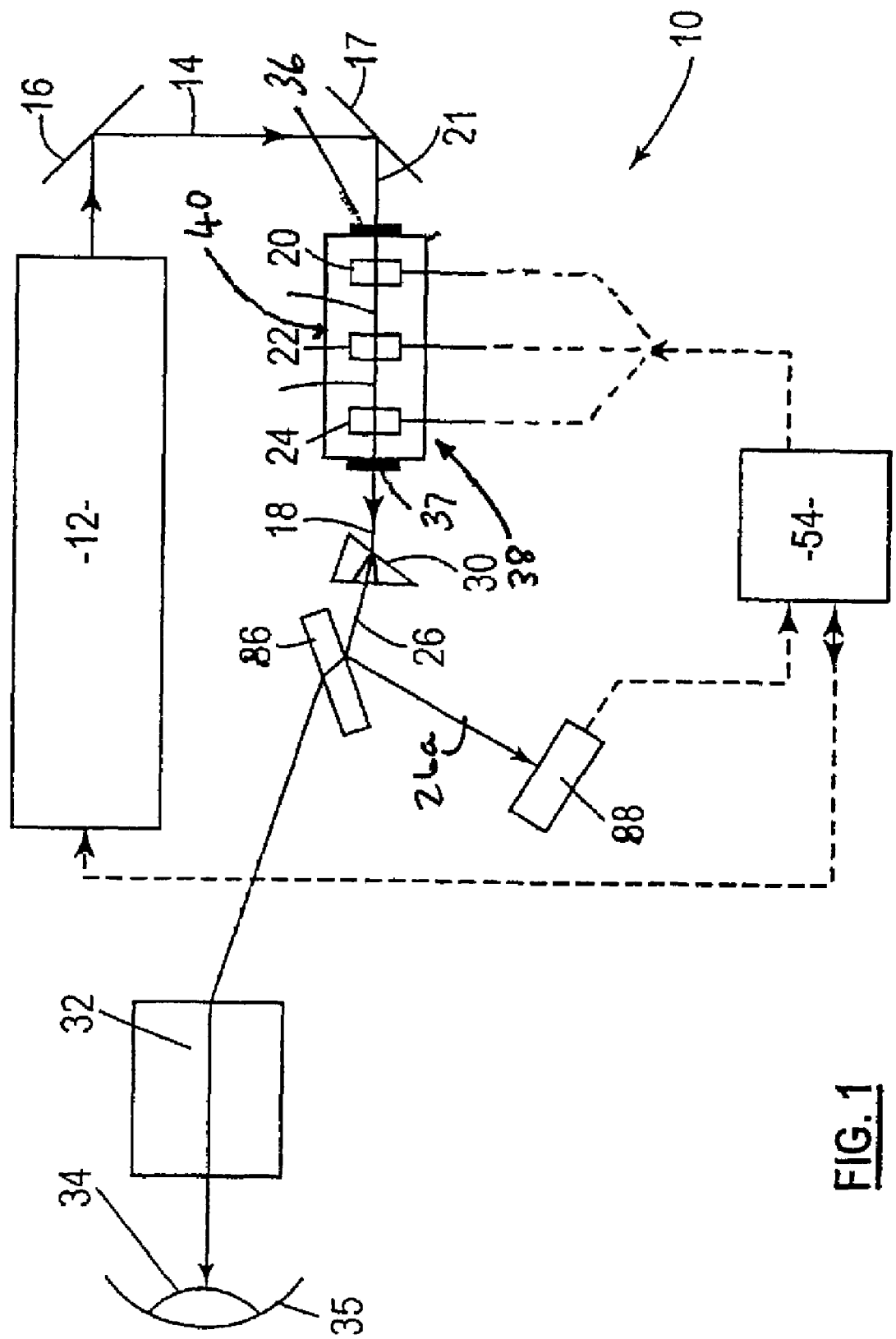
FIG. 1 is an optical diagram of an opthalmic laser beam generation system incorporating an embodiment of the invention.
Figure 2:
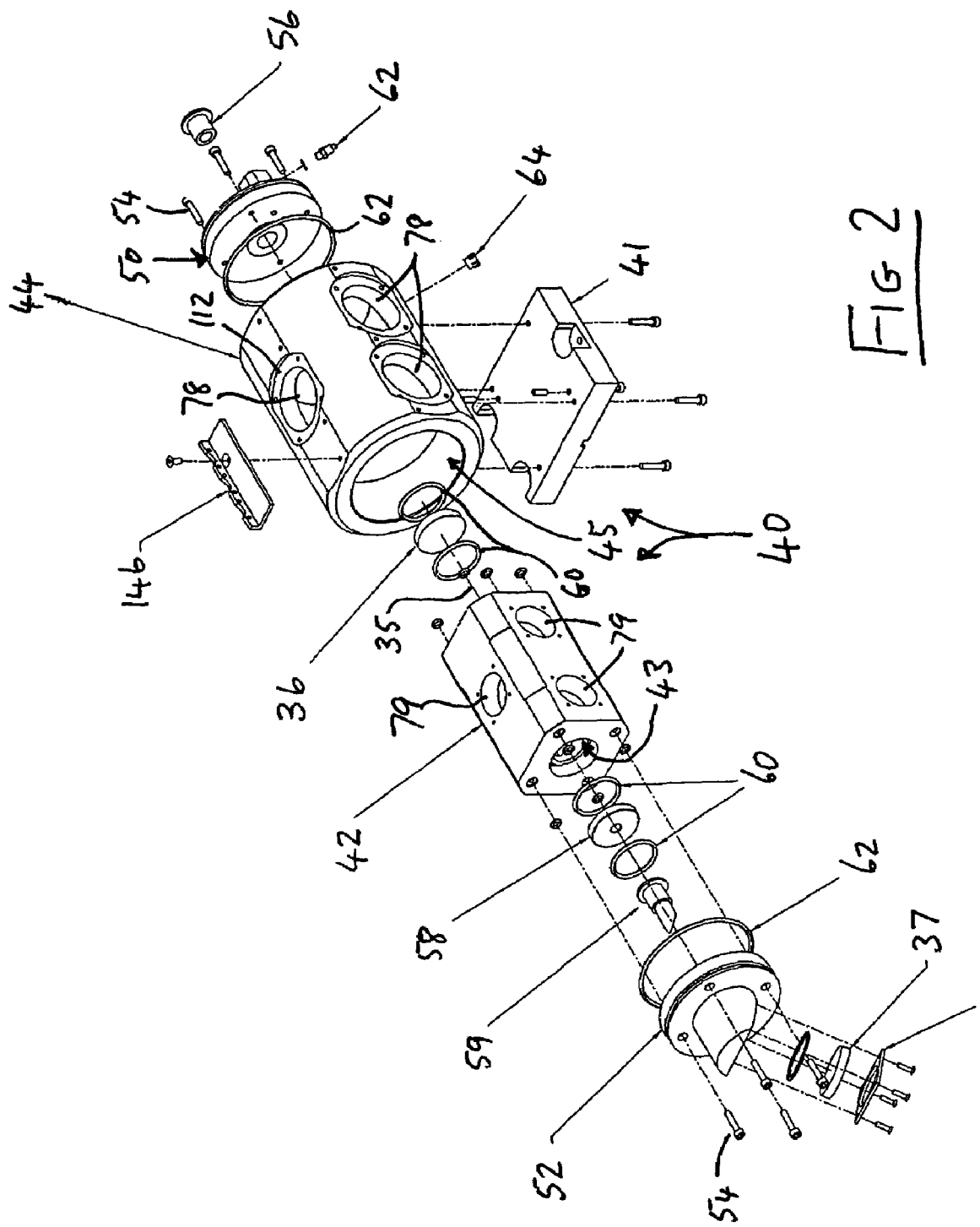
FIG. 2 is an exploded isometric view of the crystal housing apparatus of the laser beam generating system of FIG. 1, which apparatus is an embodiment of the invention.

An optical diagram for an ophthalmic laser beam generation system 10 is depicted in FIG. 1. The system 10 includes a solid state laser 12 that emits a primary laser beam 14 in the infra-red region of the electromagnetic spectrum. Primary laser beam 14 is guided by optical elements, in this case mirrors 16, 17, along an optical alignment or axis 21, through a series of non-linear optical (NLO) crystals 20, 22, 24 from which emerges a multi-component output beam 18. Beam 18 comprises the original beam 14 and several harmonics generated by crystals 20, 22, 24. The desired harmonic is separated out by a prism 30, or a by dichroic mirror arrangement.

In an application for refractive eye surgery by photo-ablation, beam 26 is directed by a beam delivery system 32 onto the cornea 34 of an eye 35.

NLO crystals 20, 22, 24 are mounted within a protective housing 40 of crystal housing apparatus 38 of the form illustrated in FIGS. 2 to 5, and aspects of their environment are controlled by a controller 54. In this case, controller 54 also operates laser 12 but a separate controller might be used for this purpose. A small portion 26a of beam 26 is diverted by a beamsplitter 86 to a photo-detector 88, such as a photodiode, for measuring and monitoring the energy of beam 26.

A particularly suitable laser 12 is a Q-switched neodymium:YAG laser producing a 2-10 mm pulsed laser beam 14 of fundamental wavelength 1064 nm. The beam 14 is collimated, resulting in a collimated harmonically generated beam downstream. Pulse energies for the fundamental wavelength typically range from 10 to 30 mJ per pulse in the practice of the present invention. More conventionally, much higher energies per pulse, eg up to 1000 mJ, are typical. A variety of other laser sources are suitable but preferred sources are $Nd^{3+}$ doped laser media such as Nd:YLF, Nd:glass and $Nd:YV0_4$.

A particularly effective and convenient crystal set 20, 22, 24 is as follows. Crystal 20 is a LBO crystal that uses type I or type 11 phase matching as a frequency doubling unit to generate a frequency doubled beam 15 of second harmonic wavelength 532 nm. Instead of a LBO crystal, crystal 20 may alternatively be KTP, BBO, KD*P or any other suitable NLO crystals. The other two crystals 22, 24 are preferably CLBO crystals although other suitable crystals include BBO, and KD*P and related isomorphs. Crystal 22 converts frequency doubled beam 15 at 532 nm to a beam 23 of 4th harmonic wavelength 266 nm, utilising type I phase matching. In crystal 24, beam components 15 and 23, of fundamental and fourth harmonic wavelengths respectively, are frequency mixed to produce a laser beam component 26 of the fifth harmonic wavelength, 213 nm. This is effected by means of sum frequency generation, a type I phase matching interaction.

Reverting now to FIGS. 2 to 5, crystal housing apparatus 38 will be described in detail.

Housing 40 rests on a base 41 and is generally elongate and of largely cylindrical external appearance, extending from a laser entry window 36 at one end to an exit window 37 at the other. The centre line connecting the windows defines the optical alignment or optical axis 35 of the housing. The entry window 36 consists of a coated BK7 or coated fused silica substrate, while exit window 37 consists of an uncoated Suprasil (fused silica) substrate that is fixed relative to optical axis 35 on the Brewster angle for 213 nm incident light. Light reflected from exit window 37 is deflected to a beam dump (not shown).

Housing 40 is of a double-sealed structure comprising an inner body 42 and an outer cylindrical body 44. Body 44 is open-ended and hollow, thereby defining an outer chamber 45 which is hermetically sealed with respect to the exterior, and which in turn houses inner housing body 42. Inner housing body 42 has a through-bore open at each end that defines an inner chamber 43, which is hermetically sealed with respect to sub-chamber 45 and itself houses the three crystals 20, 22, 24.

Hermetic sealing of inner chamber 43 is effected by respective end caps 50, 52 that are fitted with windows 36, 37 and are fastened to the ends of inner body 42 by respective screw sets 54, to clamp within the end caps respective optical shield elements 56 (at the entry end), and 58, 59 (at the exit end) with appropriate O-rings 60. The two end caps 50, 52 are received within the ends of outer housing body 44 and carry further O-rings 62, to hermetically seal the ends of outer chamber 45.

Vacuum quick-connect couplings 62, 64 are fitted to end cap 36 and to the cylindrical surface of outer housing body 44 adjacent one end, for connection to vacuum lines for evacuating chambers 43, 45. The preferred pressure in chamber 43 is less than 0.5 atmosphere, preferably less than 0.1 atmosphere. Typically, the vacuum pump may be driven by feedback from a pressure sensor (not shown) in chamber 43 to maintain the vacuum at the desired range or level.

Crystals 20, 22, 24 are supported in holders 70, 72, 74 that project cantilever-like into chamber 43 from respective mountings 86 that are fitted, in a hermetically sealed manner by means of O-rings 116, in respective openings 78 in matching seats 112 in the side walls of outer body 44 and in its bottom wall 59, and in registered apertures 79 in inner body 42. All of the holder/mounting units are of similar construction and it is therefore proposed to describe only one of them, holder 74, in detail, with particular reference to FIGS. 4 and 5.

The principal structural component of holder 74 is an integral open-topped barrel 100 having a floor 102 and disc-like end walls 104, 105. One end wall 104 has a co-axially projecting tubular conduit 103 which extends through its respective aperture 79 and opening 78 (FIG. 2), in which it is rotationally supported by inner and outer bosses 106, 107 and bushes 108, 109. O-ring sets 110, 111 hermetically seal the conduit 103 to the respective bosses and this sustains the vacuums in chamber 43, 45. Lead conduits 103 are rotatable in their bushes to orient the crystals.

Barrel 100 is biased against inner boss 106 by helical compression spring 135, held in collar 136 on end wall 105 of the barrel, on a stud 118 that engages the wall of inner body 42.

Outer boss 107 is clamped into position in a matching seat 112 (FIG. 3) in outer body 44 by screws 114, the engagement hermetically sealed by O-ring 116 in groove 117.

Crystal 24 (FIG. 5) fits into a cavity 25 defined by a U-shaped seat 122 of generally rectangular form on a Peltier heater unit 120. The open end of cavity 25 is closed by a seat wafer 124, and the sides by respective ceramic shields 126a, 126b fastened in turn to the side faces of a thrust pad body 128 that receives and fits about U-shaped seat 122 and is fixed by screws 129 onto end shoulders 131 of barrel 100. The crystal position is maintained without mechanical clamping of the crystal by a helical compression spring 130 that locates in an aperture 132 in that pad body 128 and acts on seat wafer 124.

Figure 3:
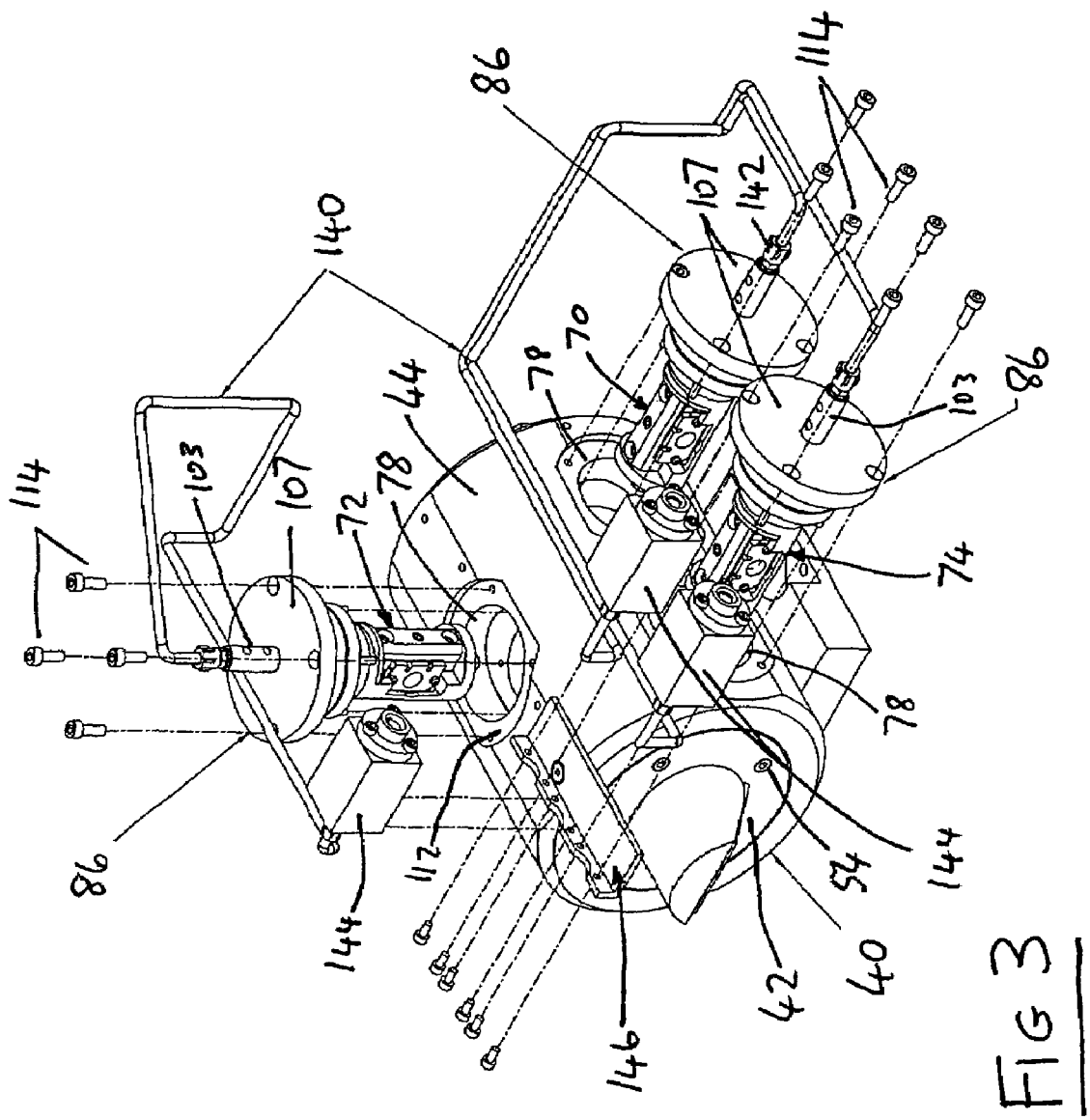
FIG. 3 is an assembled view of the crystal housing apparatus, with the crystal holders shown extracted from the housing.
Figure 4:
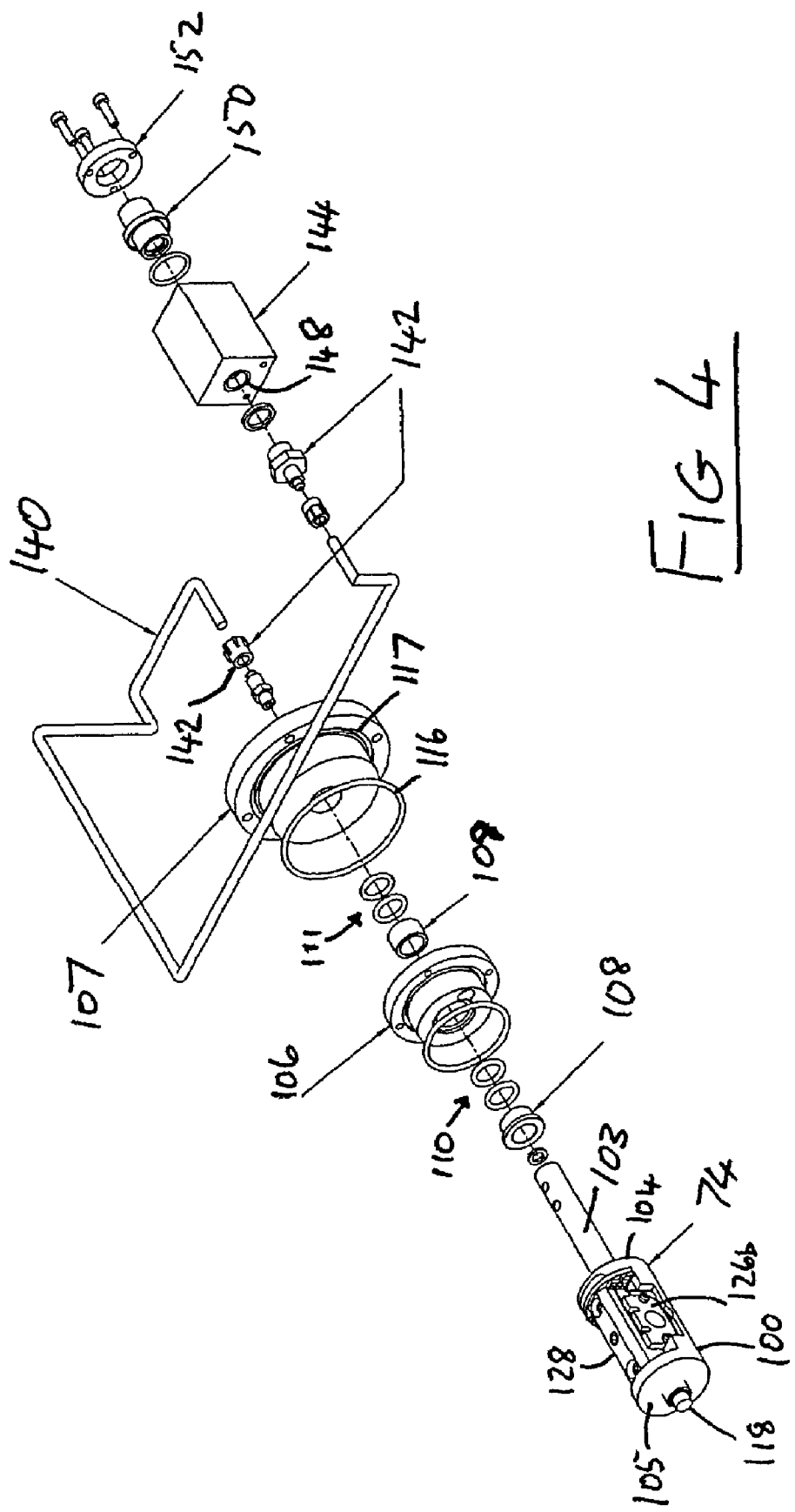
FIG. 4 is an exploded view of an individual crystal holder with its attendant structures.
Figure 5:
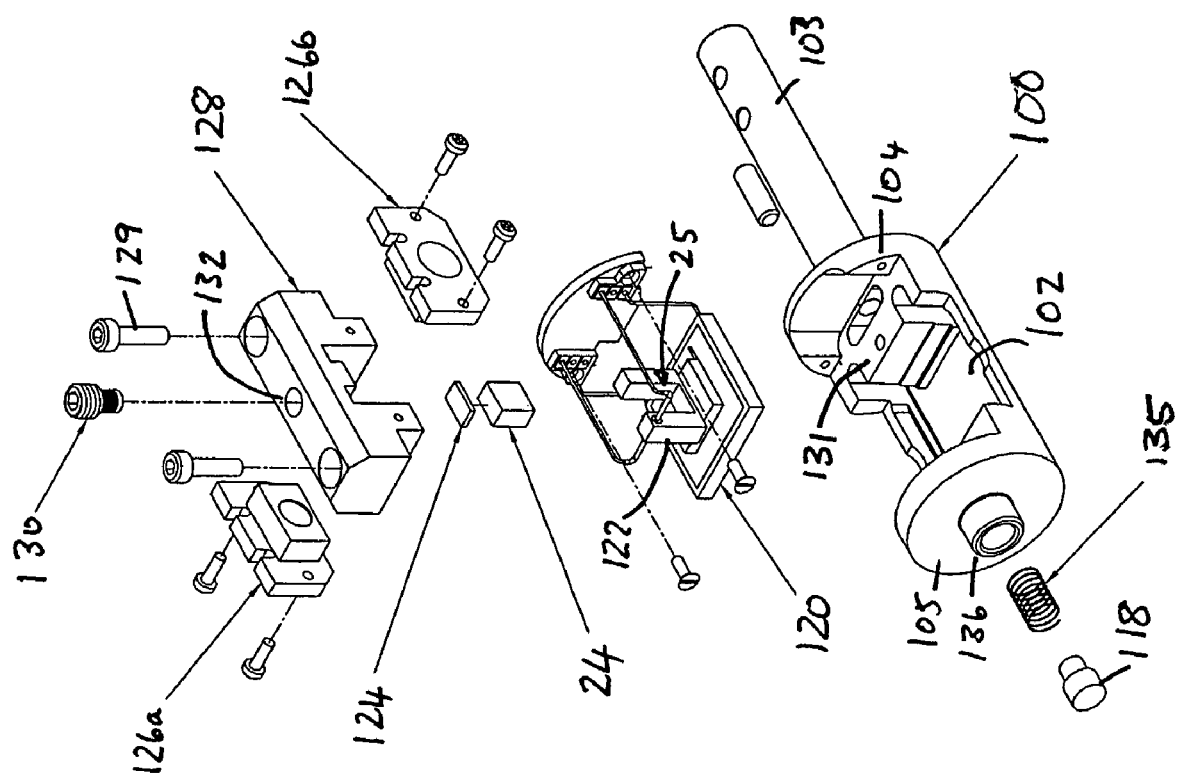
FIG. 5 is an exploded view of the holder arrangement for retaining each crystal in position.

Peltier heater unit 120 seats neatly in barrel 100 on to floor 102. Electrical leads for the heater unit, and for a thermostat (not shown) that engages and measures the temperature of crystal 24, are led to the exterior of the housing via conduit 103, a vacuum tube 140 coupled to the outer end of conduit 103 by a quick-connect coupling 142, and a sealing body 144 (FIG. 3).

The three vacuum sealing bodies 144 for the respective crystal holders are mounted side-by-side to a mount plate 146 on the exterior of outer housing body 44. Each sealing body 144 is a rectangular box. Vacuum tube 140 is sealingly attached to an aperture 148 (FIG. 4) at one end, and a sealing plug 150 retained by a sealing cap 152 in an opening (hidden from view in FIG. 4) at the other end.

For optimum crystal performance and operating life, a three-crystal set is prepared, delivered and maintained within housing 40 as a hermetically sealed evacuated package. Ideally, a vacuum will at all times be applied to couplings 62, 64, but the double-sealed construction and attention to sealing of all potential leakage paths allow maintenance of a preferred vacuum in chamber 43 for extended periods, even without an applied vacuum source.

Preferably, the crystals are also maintained with accuracy at selected temperature ranges by operation of Peltier heater units 120, and monitoring of the associated thermostats.

Preferred crystal temperatures are as follows:

| | |
|---|---|
| LBO crystal 20 | 40° C. |
| CLBO crystals 22, 24 | 130° C. |

These temperatures are preferably maintained to ±0.2° C. It is thought that maintenance of a vacuum in chamber 43, preferably in the range 0.05 to 0.5 atmospheres, prevents or minimises water vapour re-absorption by the NLO crystals: it is believed that this reduces the cyclic process that has previously degraded the performance and operating life of NLO crystals, or at least reduces the adverse effect of the cyclic process. This accurate maintenance of temperature is especially important for the LBO crystal, which must be held at a very stable pre-set temperature to maintain alignment.

It is further believed that this improvement is further enhanced by having the three NLO crystals, in this case the LBO and two BBO crystals, in a single evacuated chamber, ie. in a uniform evacuated environment, rather than in discrete single-crystal housing units. One chamber facilitates alignment and simplifies provision of a vacuum. Long-term uniformity of crystal temperatures with minimal vacuum further assists a favourable outcome.

A further advantage of a single chamber is the elimination of windows between the crystals: these windows would cause substantial losses, as high as 50% in aggregate. Optimum relative crystal orientation is set, in either automatic or manual feedback, to produce a peak signal for the desired harmonic at downstream off-line photodetector 88, which signal is fed to controller 54.

The invention claimed is:

1. Apparatus for effecting harmonic conversion of a laser beam of predetermined frequency to provide plural harmonic components of the laser beam at frequencies different from said predetermined frequency, said apparatus comprising:
   a housing defining a hermetically sealed chamber able to be maintained at a pressure below atmospheric pressure;
   port components configured to evacuate said chamber;
   a plurality of optical components configured to form an optical path for said laser beam and said components thereof through said housing and said chamber; and
   a plurality of individual holders for retaining respective frequency conversion crystals at spaced locations in said optical path,
   wherein said housing is a double-sealed housing having said chamber containing the crystals and an outer sub-chamber, which chamber and sub-chamber are separately hermetically sealed.

2. Apparatus according to claim 1, further comprising components for heating each of said crystals individually in said chamber, components for monitoring the temperature of each crystal, electrical communication lines for communicating said heating components and monitoring components to the exterior of the housing, and hermetic access porting through which said communication lines pass substantially without diminishing the vacuum in said chamber.

3. Apparatus according to claim 1, wherein said individual holders for the crystals are individually rotatable to finely adjust the orientations of the respective crystals.

4. Apparatus according to claim 1, further comprising non-linear optical (NLO) crystals in said respective individual holders.

5. Apparatus according to claim 4, wherein said NLO crystals include one or more caesium lithium borate (CLBO) crystals.

6. Apparatus according to claim 1, wherein each of said holders includes components for clamping its respective crystal in at least two directions.

7. Apparatus according to claim 6, wherein said at least two directions comprise a first direction perpendicular to the optical alignment and a second direction substantially coaxial with or at least parallel to the optical alignment.

8. Apparatus according to claim 6, wherein said clamping components for each crystal is arranged to minimize stress on the respective crystal and to distribute the clamping force over a large area of the crystal.

9. A laser beam generation system comprising apparatus according to claim 1, for generating said laser beam, and optics to direct the generated laser beam to said apparatus.

10. A system according to claim 9, wherein said laser components comprises solid state laser generation components.

11. Laser ablation apparatus incorporation a laser beam generating system according to claim 9.

12. Laser ablation apparatus according to claim 11, configured as apparatus for performing refractive eye surgery by photo-ablation of corneal or other eye tissue.

* * * * *